United States Patent [19]

Krumeich et al.

[11] Patent Number: 5,011,498

[45] Date of Patent: Apr. 30, 1991

[54] CUTTING APPARATUS FOR THE CUTTING OF A ROUND CORNEAL DISC

[76] Inventors: Jorg H. Krumeich, Propst-Hellmich-Promenade 28, 4630 Bochum 6; Norbert Quast, Gantenberg Strasse 18, 4300 Essen, both of Fed. Rep. of Germany

[21] Appl. No.: 465,052

[22] Filed: Jan. 16, 1990

Related U.S. Application Data

[63] Continuation of Ser. No. 164,589, Mar. 7, 1988, abandoned.

[30] Foreign Application Priority Data

Mar. 5, 1987 [DE] Fed. Rep. of Germany ....... 3707004

[51] Int. Cl.⁵ ............................................. A61B 17/32
[52] U.S. Cl. ................................................... 606/166
[58] Field of Search ................ 606/166, 161, 179, 180

[56] References Cited

U.S. PATENT DOCUMENTS

| | | | |
|---|---|---|---|
| 3,058,471 | 10/1962 | Shope | 128/305 |
| 3,074,407 | 1/1963 | Moon et al. | 128/308 R |
| 4,205,682 | 6/1980 | Crock et al. | 128/305 |
| 4,236,519 | 12/1980 | La Russa et al. | 128/305 |
| 4,429,696 | 2/1984 | Hanna | 128/310 |

Primary Examiner—Michael H. Thaler
Attorney, Agent, or Firm—Clifford A. Poff

[57] ABSTRACT

Cutting apparatus for excision of a round corneal disc. The cutting apparatus includes a hollow cylindrical cutting knife known as a trepan. The cutting knife is held by an outer cylinder which has a connection plate on its end extending toward the cornea to be cut. Extending perpendicularly to the axis of the cylinder is a connection plate with a bore for the passage of the cutting knife. In the cylinder there is situated near its rear end a clip ring, within which the rear end of the cutting knife is held by a frictional fit. With the aid of a feed apparatus, the cutting knife is axially moveable with respect to the cylinder for the performance of the cutting movement. The cutting apparatus can be joined with its connection plate either by an artificial anterior chamber support or with a vacuum ring on the patient eye. In both cases, there is assured guiding of the cutting knife perpendicularly to a plane which traverses the base of the cornea. With such an apparatus, it is possible, first to obtain cuts running through the outer surface of the cornea running perpendicularly through the outer surface of the cornea and moreover to obtain corneal discs from a donor eye which are taken so as to correspond exactly with the corneal discs taken from the patients eye.

22 Claims, 2 Drawing Sheets

CUTTING APPARATUS FOR THE CUTTING OF A ROUND CORNEAL DISC

This is a continuation of co-pending application Ser. No. 164,589, filed on Mar. 7, 1988, now abandoned.

BACKGROUND OF THE INVENTION

1. Field of the Invention

The invention relates to an apparatus including a hollow cylindrical cutting knife (trepan) for cutting a corneal disc from a human eye.

2. Description of the Prior Art

In ophthalmology, it is known to transplant corneal tissue from a donor eye to a patients eye. Such operations, called perforating kerataoplastic, are performed in the case of scarring or disease of the cornea which lead to an irregular cornea outer surface, whereby the image formation on the retina by the cornea is distorted when the cornea is acting as the most strongly refracting lens element of the eye. There exist the possibility of obtaining the corneal disc which is to be transplanted either from a whole donor eye or from a cornea which has been preserved in the preserving solution. In the perforating kerataoplastic the cornea is installed in a concave support and a corneal disc to be transplanted is carved out with the aid of a round cutting knife, called a trepanning, from the posterior side of the endothelium of the cornea, towards the anterior, the epithelium, which abuts the support.

The trepanning on the eye of the patient is done by fixing the eye with a ring which is brought in upon the eutis vera or corium of the eye for stabilization of the cornea shape. Most recently, there have been conducted also some fixations with the aid of the vacuum ring lying against the eye. For the trepanning, a handheld, hand-operated or motor-operated trephine is brought against the cornea and the corneal disc is cut out by rotation.

These methods have a serious drawback, in that it is not possible to obtained identical corneal discs from the donor eye on the one hand and the patient's eye in the other. This has various causes. The trephining operation is influenced by the elasticity and the resistance of the cornea to the cutting movement by the trephine. Moreover, the penetrating cuts, which are made from the front, to the posterior of the cornea are broader, i.e., larger in diameter, at the exit place than at the entrance location, so that the cutting surface is not perpendicular to the surface of the endothelium, but rather angled, or inclined. Thereby, one obtains in the trephining operation from the posterior side of a cornea a greater diameter at the anterior exterior surface of the cornea and conversely in the trephining operation on the patient eye one obtains a greater diameter on the inner side or surface of the cornea. The fitting together of the donated cornea disc in a patients' eyes is according to this method possible only by pressing together of the tissue.

Moreover, a free-hand guided trepan, such as it is used on the patient's eye, cannot by grinded exactly perpendicularly to the outer surface. Also, the eye moves during the trephining operation, and as the depth of cut increases, a lesser cutting resistance is encountered due to the lower opposition by the eye's inner pressure opposing the trepan as compared to the original pressure. The mobility of the eye leads easily to a departure of the trephine position from the desired perpendicular direction for the plane of the limbus of the cornea. An angular holding of the trepan has an equally adverse affect. A mathematical calculation of the affect on angled holding of the trepan yields, even with a departure of 10 degrees, a difference of more than 4 dioptres in the two corneal planes. The consequence of this is that even with well conducted trephining operations, with an angled departure of no more than 5 degrees from the perpendicular of the donor eye and an equal departure in the eye of the receiver, the effect of the angled portion values can become accumulative and produce the above indicated astigmatism. Angled departures of the trephine of 10 to 15 degrees from the vertical plane, which cause astigmatisms of 10 diopters, are therefore not rare.

SUMMARY OF THE INVENTION

The present invention is helpful in this regard by addressing the problem of providing a cutting apparatus for the cutting out of a corneal disc with the use of a hollow cylindrical cutting knife, with the aid of which it is possible to guide the cutting knife during the cutting operation exactly perpendicular to a plane which traverses the limbus of the cornea, that is, the base of the cornea. Moreover, with the use of this cutting apparatus, it is possible to obtain cuts from both donor eye a patient's eye, that run perpendicularly to the outer surface of the cornea.

This problem is solved according to the present invention by providing a cutting apparatus for the excision or cutting of a corneal disc from a human eye, the apparatus including: a hollow cylindrical cutting knife having a longitudinal central cylinder axis; an exterior cylinder including on its end adjacent to the cornea during excision of a corneal disc a planar connection plate having a bore therethrough, the connection plate extending perpendicular to the cylinder axis; a clip ring guidingly situated in a rear end portion of the cylinder for holding the cutting knife by a frictional fit; and feed apparatus held on the cylinder by the clip ring for moving the cutting knife with respect to the cylinder to provide an axial feed of the cutting knife.

Advantageously, the feed apparatus includes: a round piston with a central bore held in the cylinder; a guide cylinder immovably situated in the bore of the piston which on the one hand bears upon the inner wall of the cutting knife and on the other hand exhibits a projecting end with exterior threading opposite of the piston; a turning ring threadedly engaged on the exterior threading; a freely rotatably glide ring in a surrounding groove in an exterior wall of the guide ring; and a plurality of projections with parallel axis extending axially through the piston, each of the projections being movable in a bore and with their inner ends connected with the clip ring. Preferably, the cutting apparatus further includes a guide cylinder including a handwheel at the outer end thereof. The guide cylinder is preferably provided with a central bore therethrough. The cutting apparatus preferably further includes a piston with a planar end surface extending perpendicularly to the cylinder axis on an inner end of the cylinder, the planar end surface before the beginning of a cutting operation being flush with the cutting edge of the cutting knife. The clip ring has a slit in the wall thereof extending in a direction of the axial length of the clip ring. The cylinder and the connection plate can be integral. Also, the connection plate contains a plurality of diametrically opposed bores therethrough. However, the connection plate must include opposed connection elements on outer sides thereof.

For the obtaining of the corneal disc from a donor cornea, there is regularly used a known apparatus for the holding of the corneal disc by which the cornea lies upon a support as provided with a round support having an opening and capable of being pressed with a ring-shaped all-sided container, whereby it is possible with a pressure medium to fill the hollow space between the support and the retained cornea disc. The cutting apparatus is, with its connection plate, fastened to this apparatus in such a manner as indicated above that the cutting knife is located centrally with respect to the retained corneal disc. In order to obtain a perpendicular cut with such a trephining operation, i.e., a cut perpendicular to the surface of the cornea, it is useful according to a further embodiment of the invention to form the guide cylinder on its inner ends as a piston with planar surfaces at its end extending perpendicular to the cylinder axis, which are, before the beginning of a cutting operation, in the same plane or flush with the cutting edge of the knife. The cutting knife and inner piston are simultaneously brought down from above to the cornea whereby the cornea in the vicinity of the cutting edge of the cutting knife is brought into a planar position. From this position now the cutting knife can be further moved with the aid of the feed apparatus without the inner piston and thus the cornea can be cut perpendicularly.

For the trephining operation on the patient's eye, the cutting apparatus can be set-up according to the invention, for this purpose by first selecting and installing a kind of vacuum ring known per se against a patients eye. On the connection plate of the cutting apparatus there are for this purpose provisions made that make it possible for a problem-free conforming connection between the cutting apparatus and the vacuum ring. Advantageously, there can for this purpose be used some kind of snap fastening. Also in this case there exist the possibility of trephining the cornea either in its natural convex condition or in a position as pressed flat. In the one case, there is used a guide cylinder open on the inner end and in the other case there is used a guide cylinder that is formed on its inner end as a piston with an end surface which is perpendicular to the cylinder axis.

BRIEF DESCRIPTION OF THE DRAWINGS

These features and advantages of the present invention as well as others will be more fully understood when the following description is read in light of the accompanying drawings in which.

DESCRIPTION OF THE PREFERRED EMBODIMENT

Figure 1:
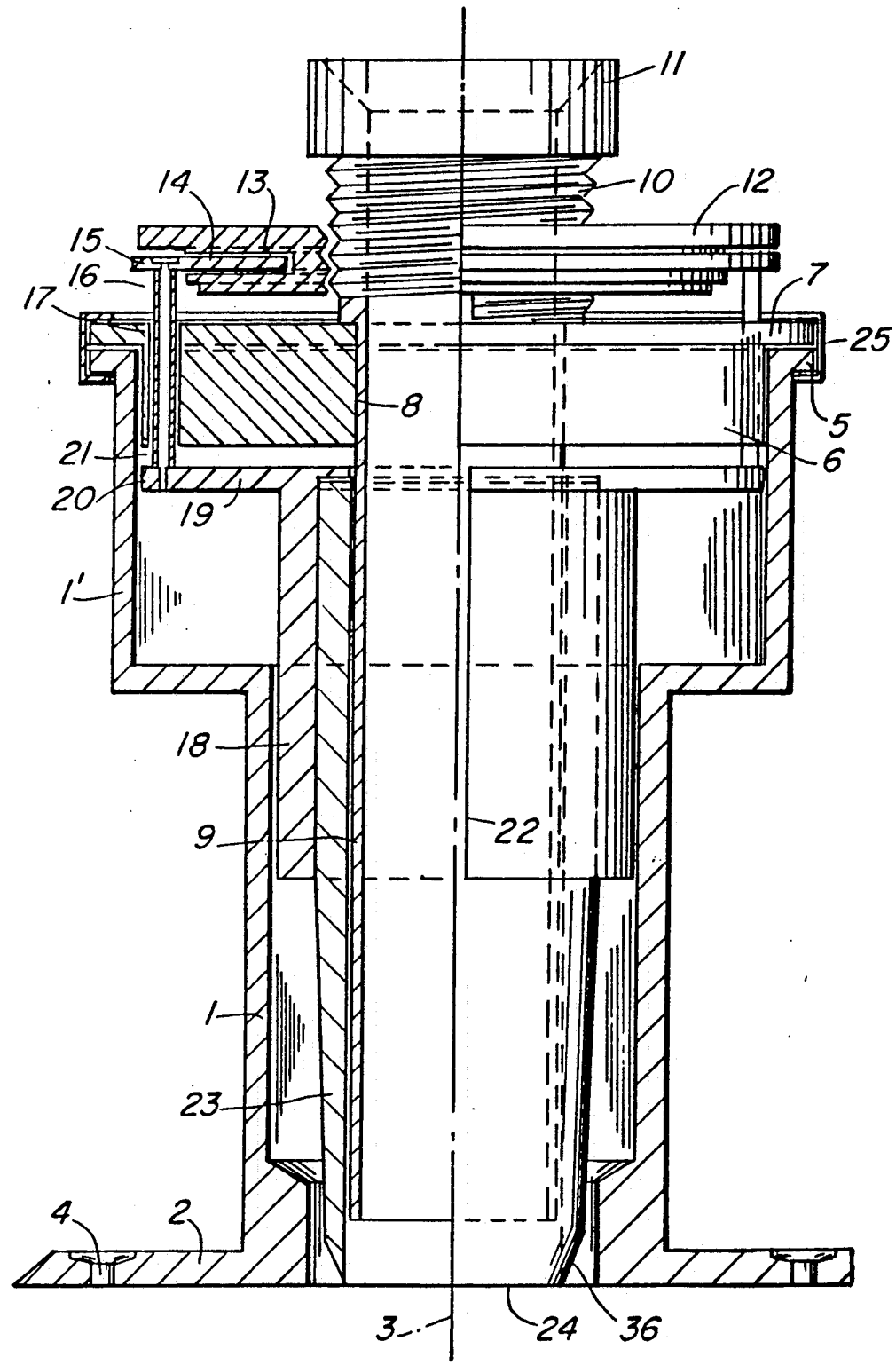
FIG. 1 is an elevation view of a first embodiment of a cutting apparatus with a hollow guide cylinder.

In the embodiment shown in FIG. 1, the exterior cylinder 1 includes a rear end section 1' with an enlarged or greater diameter as compared with front or inner end of the cylinder. On the inner end, there is formed a connection plate 2, which in the nature of a flange has a round cross section and runs perpendicularly to the central longitudinal cylinder axis 3. In the connection plate 2, there are provided a plurality, at least two bores 4 which extend through the plate 2 and are located diametrically opposite each other. With the aid of bolts, not shown, which can be installed in the bores 4, the connection plate 2 can be affixed on another apparatus, for example, onto an artificial anterior chamber seat.

Also on the rear end of the cylinder 1, there is formed a ring flange 5, the significance of which will be explained hereinafter. As the drawing shows, there is installed in the cylinder 1 at its rear end 1' a flat stopper 6, conforming to the shape of the inner surface of the rear end 1' of cylinder 1 but capable of being rotated relative thereto. The stopper 6 presses with an end-side flange 7 on the flange 5 of the cylinder 1. In a central bore 8 of the stopper 6, there is retained a hollow guide cylinder 9 with a force fit. The cylinder 9 extends with its inner end to the vicinity to the connection plate 2. A section of the guide cylinder 9 located outwardly beyond the stopper 6 is provided with a greater wall thickness and contains an external thread 10. The external thread 10 extends to and end section 11 having a cylindrical surface that performs the function of a hand wheel.

Threadedly engaged with the exterior threading 10 is a turning ring 12 having a radially extending surrounding groove 13 in which a flat disc-like glide ring 14 is freely rotatably supported. In the glide ring 14, there are contained a plurality, at least two, diametrically opposed packed bores 15, which receive cylindrical heads of each of the threaded rods 16. The stopper 6 contains a corresponding number of aligned bores 17, into each of which there is led a threaded rod 16.

In an axial extension of the stopper 6, there are located on the inside of the cylinder 1 a clip ring 18 with a rearward flange ring 19. This flange ring 19 contains in extension of the threaded shaft 16 aligned threaded bore 20, into which the free end of each threaded shaft 16 is threaded. For establishment of the particular and axial separation between the flange ring 19 and the gliding ring 14, there is positioned on each threaded shaft 16 a case or housing 21, which is led in an axially movably fashion in the bore 17. The side wall of clip ring 18 contains in one place a through cut axis extending slit 22. This slit allows the clip ring 18, at least in its cylindrical section, the possibility of widening out and expanding at least a little bit radially, enough to bring to bear a corresponding pressure on the outer wall of a cylindrical cutting knife, as will be described herebelow, when such a knife is received therein.

The clip ring 18 serves for the holding of a hollow cylindrical cutting knife 23, which can be urged against the clip ring from the inner side and can be held in the same because of the slight expanding of the clip ring 18 which thereby provides a friction fit for the cutting knife 23. The axial length of the cutting knife 23 is selected in such a manner that when the cutting knife 23 is seated in clip ring 18 the knife cutting edge 24 is situated substantially at the plane of the surface of the connection plate 2.

The degree of coherence between the cylinder 1 and the stopper 6, which is rotatable in respect to the cylinder 1, can be influenced in various ways. In the illustrated embodiment, there are provided for this purpose U-shaped retaining rings 25.

Before the operation of the cutting apparatus, the cutting knife 23 is so operated by turning of the rotating ring 12 that its cutting edge 24 is definitely caused to correspond or to be flush with the plane of the underside of the connecting plate 2, such as it is shown in FIG. 1. By continued further turning of the turning ring 12, the cutting knife 23 is moved axially out of the cylinder 1. When the hand wheel 11 is rotated, the stopper 6 and thereby, the cutting knife 23 may be caused to execute a turning movement about the longitudinal axis 3.

Figure 2:
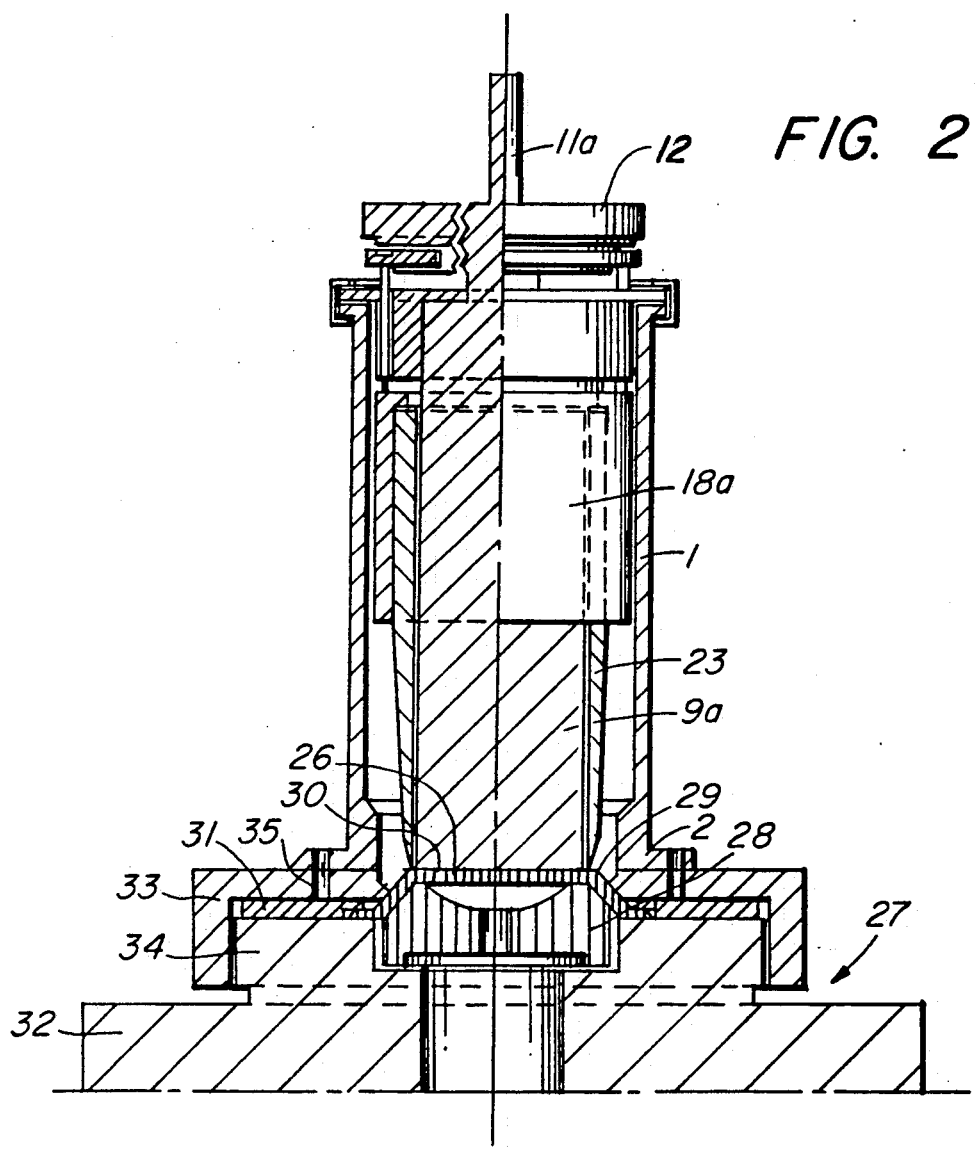
FIG. 2 is an elevation view partly in section of a second embodiment of cutting apparatus in connection with an artificial anterior chamber seat or bed.

FIG. 2 shows a modified embodiment of a cutting apparatus, which in its main principle parts corresponds entirely to the cutting apparatus shown in FIG. 1 and described hereinbefore. In FIG. 2, therefore, all of the parts that correspond to the ones according to FIG. 1 are indicated with the same reference numerals.

Otherwise than in the embodiment according to FIG. 1, in the embodiment according to FIG. 2 the cylinder 1 is formed with the same cross section throughout. A difference consists in the form of the guide cylinder 9A, which forms on its inner end a piston with a planar end surface 26 running perpendicular to the cylinder axis 3. At the rear end, i.e., in the connection to the section with the exterior threading 10, there is in this embodiment provided, in place of the turning wheel or hand wheel a turning plug or pin 11A.

FIG. 2 shows the cutting apparatus in its use in connection with an artificial anterior chamber support 27, of which only the head region is shown. This contains a cylindrical support body 28 with a central depression which is surrounded with a protruding wall 29. On the support body there lies a corneal disc 30 of a donor eye. At its edge, the corneal disc 30 is pressed with a pressure ring 31 against the upper surface of the housing 32 of the interior chamber support 27. The pressing force is produced for this purpose with the aid of a covering nut 33, which is supported on the exterior threading of cylindrical annex 34 of the housing 32. By the introduction of a pressure medium such as air or fluid into the space between the corneal disc 30 and the supporting body 28, the corneal disc 30 can be subjected to an inner pressure between the support and the wall 29, one which is corresponding to the pressure measured in the eye of the patient. In this manner, there can be produced in a donor corneal disc 30 conditions substantially the same as those in the eye of the patient.

In order to be able to affix solidly for a period of time the cutting apparatus to the interior pressure support, it is necessary to bring in the lid part of the nut 33 threaded bores 35 that are aligned with the bores 4 in the connection plate 2. With the aid of bolts, not shown, such a solid connection between the cylinder 1 and the nut 33 can be produced.

FIG. 2 shows the flush relationship between the cutting edge of the cutting knife 23 and the planar end surface 26 of the guide cylinder 9a immediately before the beginning of the corneal cutting movement. With the aid of the end surface 26 of the guide cylinder 9a, the corneal disc 30 is pressed into a planar support, as FIG. 2 shows. In the making of the cut, the cutting knife 23 is now pressed axially into the corneal tissue to the desired depth via turing of the turning ring 12. The cut is completed by rotation of turning plug 11a. Thereby there is produced a cutting angle that runs perpendicularly over the upper surface of the corneal disc 30. As the drawings show, the cut of the cutting knife 23 is so formed that only the outer surface 36 is inclined or bent, while in contrast the inner surface is formed by the cylindrical surface of the hollow cylindrical cutting knife 23.

Figure 3:
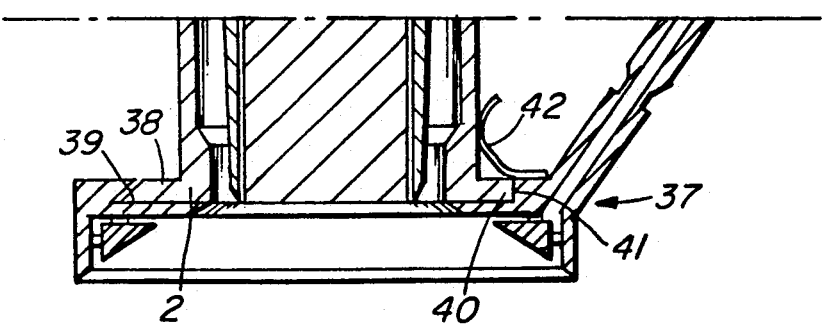
FIG. 3 is a section in the lower region of a cutting apparatus in a practice according to the embodiment of FIG. 2 in connection with a vacuum ring capable of being brought into contact with a patient's eye.

As shown in FIG. 3 for the trephining on the eye of the patient, there is first installed on the eye a vacuum ring 37, which has a ring shaped inner surface that is conformed to the outer surface of the eye. A vacuum is then produced in the intermediate space between the outer surface of the eye and the support surface which draws the ring solidly against the eye and holds it in this manner. Such a vacuum ring is known per se.

The solid connection between the cylinder 1 and the vacuum ring 37 is effected according to the embodiment of FIG. 3 by a kind of snap fastener. Therein, the connection plate 2 contains on its outer surface a projection 38, which grips into an undercut part 39 of the vacuum ring 37. On the opposing outer side of connection plate 2, there is located a planar annex 40 which conformingly abuts against a corresponding surface 41 of the vacuum ring 37. To secure the connection of the parts, there is provided on the wall of the cylinder 1 a leaf spring 42 or the like.

We claim:

1. A cutting apparatus for the excision of a corneal disc from a human eye, said apparatus including:
   a hollow cylindrical cutting knife having a longitudinal central cylinder axis;
   an exterior cylinder including on its end adjacent to the cornea during excision of a corneal disc a planar connection plate having a bore therethrough, said connection plate extending perpendicular to said cylinder axis;
   a clip ring guidingly situated in a rear end portion of said cylinder for holding said cutting knife by a frictional fit; and
   feed apparatus held on said cylinder by said clip ring, said feed apparatus including:
   a round stopper having a central bore and held in said cylinder;
   a guide cylinder fixedly retained in the central bore of the stopper, said guide cylinder bearing upon an inner wall of the cutting knife and having a projecting end with exterior threading;
   a turning ring threadedly engaged on said exterior threading;
   a freely rotatable glide ring positioned in a surrounding groove provided in an exterior wall of the turning ring; and
   a plurality of rod means having parallel axes, said rod means being attached to said glide ring and extending axially through the stopper, each of the rod means being movable in an individual one of a plurality of corresponding bores provided in said stopper, inner ends of said rod means being connected with the clip ring,
   whereby said feed apparatus operates to permit rotational as well as axial movement of said cutting knife relative to said cylinder, said rotational movement and said axial movement being performed by separate and independent manipulations of said feed apparatus.

2. A cutting apparatus for the excision of a corneal disc from a human eye, said apparatus including:
   a hollow cylindrical cutting knife having a longitudinal central cylinder axis;

an exterior cylinder having a central bore extending to its end adjacent to the cornea during excision of a corneal disc;

a clip ring guidingly situated in a rear end portion of said exterior cylinder for holding said cutting knife by a frictional fit;

feed apparatus held on said cylinder by said clip ring, said feed apparatus including:

a stopper having a central bore and held to rotate in said exterior cylinder;

a rotatable guide cylinder fixedly retained in the central bore of the stopper, said guide cylinder bearing upon an inner wall of the cutting knife and having a projecting end with exterior threading;

a turning ring threadedly engaged on said exterior threading;

a glide ring supported to freely rotate in a groove in an exterior wall of the turning ring; and means connecting said glide ring to rotate with the clip ring;

whereby said feed apparatus operates to permit rotational as well as axial movement of said cutting knife relative to said cylinder, said rotational movement and said axial movement being performed by separate and independent manipulations of said feed apparatus.

3. The cutting apparatus according to claim 2 wherein said guide cylinder includes a planar end surface extending perpendicularly to said cylinder axis, said planar end surface before the beginning of a cutting operation being positionable so as to be flush with the cutting edge of the cutting knife.

4. The cutting apparatus according to claim 2 further including a planar connection plate on the end of said exterior cylinder adjacent to the cornea during excision of a corneal disc, said planar connection plate extending perpendicular to said cylinder axis.

5. The cutting apparatus according to claim 4 wherein said connection plate contains a plurality of diametrically opposed bores therethrough.

6. The cutting apparatus according to claim 4 wherein said connection plate includes opposed connection elements on outer peripheral portions thereof.

7. The cutting apparatus according to claim 2 wherein said stopper is rotatable supported by said exterior cylinder and wherein said feed apparatus further includes a hand wheel provided on said projecting end of said guide cylinder for manipulation by an operator.

8. The apparatus of claim 7 wherein said means for connecting said glide ring with the clip rings are axially movable relative to said stopper, whereby, during a corneal disc excision operation, said hand wheel and said turning ring are at all times and in all positions accessible and independently manipulable by an operator.

9. The apparatus of claim 8 wherein both said hand wheel and said turning ring possess surfaces which are directly accessible and manipulatable by an operator's hand.

10. The apparatus of claim 8 wherein said clip ring, said glide ring, and said turning ring are arranged coaxially with said central cylinder axis.

11. The apparatus according to claim 2 further comprising:

eye support structure adapted to be provided on an eye of a patient;

donor cornea support structure adapted to receive a donor cornea; and means for releasably attaching said cylinder to either said support structure, said means for releasably attaching immobilizing said cylinder relative to either said support structure during a cutting operation of said cutting knife on either a patient cornea or a donor cornea to thereby produce a precisely duplicated cut in both the patient cornea and the donor cornea.

12. The cutting apparatus according to claim 11 wherein said means for releasably attaching is carried on an end of said cylinder positioned closest to said cornea during excision of said disc therefrom 13. The cutting apparatus according to claim 12 wherein said means for releasably attaching comprise connection plate means projecting radially outwardly from said end adjacent to the cornea of said exterior cylinder.

14. The cutting apparatus according to claim 13 wherein said means for releasably attaching further comprise a plurality of bores passing through said connection plate means for alignment with a plurality of corresponding bores provided in said corresponding bores are in alignment, fastener means are inserted into the aligned bores for attaching the cylinder to the support structure.

15. The cutting structure according to claim 13 wherein said means for releasably attaching further comprise cooperating snap fastening means provided on said connection plate means and on said support structure.

16. The cutting apparatus according to claim 13 wherein said cooperating snap fastening means comprise mating surfaces provided on both said connection plate means and said support structure, and spring means carried by said support structure for retaining said mating surfaces in mating relationship.

17. A cutting apparatus for the excision of a corneal disc from a human eye, said apparatus comprising:

a hollow cylindrical cutting knife having a longitudinal central cylinder axis;

an exterior cylinder including on its end adjacent to the cornea during excision of a corneal disc a planar connection plate having a bore therethrough, said connection plate extending perpendicular to said cylinder axis;

a clip ring guidingly situated in a rear end portion of said cylinder for holding said cutting knife by a frictional fit;

means for rotating said cutting knife operatively connected to said clip ring, said means for rotating including a rotatable stopper having a central bore therethrough and guide cylinder fixed in said central bore of said stopper, said guide cylinder having a handwheel on an exposed outer end thereof adapted for manipulation by an operator; and means for axially moving said cutting knife operatively connected to said clip ring, said means for axially moving comprising first means threadedly engaged with said guide cylinder for axially adjusting the position of said cutting knife relative to said means for rotating, whereby manipulation of said handwheel causes rotation of said cutting knife and separate manipulation of said first means causes axial movement of said cutting knife.

18. A cutting apparatus for the excision of a corneal disc from a human eye, said apparatus comprising:
a hollow cylindrical cutting knife having a longitudinal central cylinder axis;
an exterior cylinder including on its end adjacent to the cornea during excision of a corneal disc a planar connection plate having a bore therethrough, said connection plate extending perpendicular to said cylinder axis;
a clip ring guidingly situated in a rear end portion of said cylinder for holding said cutting knife by a frictional fit, said clip ring having a slit in the wall thereof extending in a direction of the axial length of the clip ring;
means for rotating said cutting knife operatively connected to said clip ring, said means for rotating including a rotatable stopper having a central bore therethrough and a guide cylinder fixed in said central bore, said guide cylinder having a handwheel on an exposed outer end thereof adapted for manipulation by an operator; and
means for axially moving said cutting knife operatively connected to said clip ring, said means for axially moving comprising first means threadedly engaged with said guide cylinder for axially adjusting the position of said cutting knife relative to said means for rotating,
whereby manipulation of said handwheel causes rotation of said cutting knife and separate manipulation of said first means causes axial movement of said cutting knife.

19. A cutting apparatus for the excision of a corneal disc from an eye, said apparatus comprising:
a hollow cylindrical cutting knife having a longitudinal central cylinder axis;
an exterior cylinder including on its end adjacent to the cornea during excision of a corneal disc a planar connection plate having a bore therethrough, said connection plate extending perpendicular to said cylinder axis;
means situated in said cylinder for holding said cutting knife;
means for rotating said cutting knife operatively connected to said means for holding said cutting knife; and
means for axially moving said cutting knife operatively connected to said means for holding said cutting knife, said means for axially moving comprising first means threadedly engaged with said means for rotating for axially adjusting the position of said cutting knife relative to said means for rotating, said means for axially moving further comprising second means for connecting said first means to said means for holding, said second means being supported to rotate with and axially move relative to said means for rotating, wherein said means for holding, said means for rotating, and said means for axially moving are arranged coaxially with said central cylinder axis;
whereby manipulation of said means for rotating causes rotation of said cutting knife and separate manipulation of said first means causes axial movement of said cutting knife and, during a corneal disc excision operation, said means for rotating and said first means are at all times and in all positions accessible and independently manipulatable by an operator.

20. A system for the excision of a disc from an cornea, said system comprising;
a hollow cylindrical cutting knife having a longitudinal central cylinder axis;
an exterior cylinder;
means situated in said cylinder for holding said cutting knife;
means for rotating said cutting knife operatively connected to said means for holding said cutting knife;
means for axially moving said cutting knife operatively connected to said means for holding said cutting knife, said means for axially moving comprising first means threadedly engaged with said means for rotating for axially adjusting the position of said cutting knife relative to said means for rotating, whereby manipulation of said means for rotating causes rotation of said cutting knife and separate manipulation of said first means causes axial movement of said cutting knife;
eye support structure adapted to be provided on an eye of a patient;
donor cornea support structure adapted to receive a donor cornea; and
means for releasably attaching said cylinder to either said support structure, said means for releasably attaching comprising planar connect in plate means having a central bore therethrough and carried on and projecting radially outwardly from an end of said exterior cylinder positioned closest to said cornea during excision of said disc therefrom, said means for releasably attaching immobilizing said cylinder relative to either said support structure during a cutting operation of said cutting knife on either a patient cornea or a donor cornea to thereby produce a precisely duplicated cut in both the patient cornea and the donor cornea;
said means for releasably attaching further comprising a plurality of additional bores passing through said connection plate means for alignment with a plurality of corresponding bores provided in said donor cornea support structure, whereby at such time when said plurality of additional bores and said corresponding bores are in alignment, fastener means are inserted into the aligned bores for attaching the cylinder to the donor cornea support structure;
said means for releasably attaching further comprising cooperating snap fastening means provided on said connection plate means and on said eye support structure, said cooperating snap fastening means comprising mating surfaces provided on both said connection plate means and said eye support structure, and a spring means carried by said cylinder for retaining said mating surfaces in mating relationship, said mating surfaces including a projection formed along a portion of a periphery of said connection plate means, an undercut provided on said eye support structure for receiving said projection, an annex formed along said periphery of said connection plate means generally opposite said projection, and a seating surface provided on said eye support structure for receiving said annex.

21. A system including apparatus for excision of a disc from an cornea and structure for supporting said apparatus, said system comprising;
a cornea cutting device including an exterior cylinder having a longitudinal central axis, and a hollow cylindrical cutting knife carried within said cylinder;

eye support structure adapted to be provided on an eye of a patient;

donor cornea support structure adapted to receive a donor cornea; and means for releasably attaching said cylinder to either said support structure, said means for releasably attaching comprising planar connection plate means carried on and projecting radially outwardly from an end of said cylinder positioned closest to said cornea during excision of said disc therefrom, said means for releasably attaching immobilizing said cylinder relative to either said support structure during a cutting operation of said cutting knife on either a patient cornea or a donor cornea to thereby produce a precisely duplicated cut in both the patient cornea and the donor cornea;

said means for releasably attaching further comprising cooperating snap fastening means provided on said connection plate means and on said eye support structure, said cooperating snap fastening means comprising mating surfaces provided on both said connection plate means and said eye support structure, and spring means carried by said cylinder for retaining said mating surfaces in mating relationship, said mating surfaces including a projection formed along a portion of a periphery of said connection plate means, an undercut provided on said eye support structure for receiving said projection, an annex formed along said periphery of said connection plate means generally opposite said projection, and a seating surface provided on said eye support structure for receiving said annex.

22. A system for excision of a disc from a cornea, said system comprising;

an exterior cylinder having a longitudinal central cylinder axis;

a hollow cylindrical cutting knife carried within said cylinder;

eye support structure adapted to be provided on an eye of a patient;

donor cornea support structure adapted to receive a donor cornea;

means for releasably attaching said cylinder to either said support structure, said means for releasably attaching immobilizing said cylinder relative to either said support structure during a cutting operation of said cutting knife on either a patient cornea or a donor cornea to thereby produce a precisely duplicated cut in both the patient cornea and the donor cornea;

means situated in said cylinder for holding said cutting knife;

means for rotating said cutting knife operatively connected to said means for holding said cutting knife; and means for axially moving said cutting knife operatively connected to said means for holding said cutting knife, said means for axially moving comprising first means threadedly engaged with said means for rotating for axially adjusting the position of said cutting knife relative to said means for rotating, said means for axially moving further comprising second means for connecting said first means to said means for holding, said second means being supported to rotate with and axially move relative to said means for rotating, wherein said means for holding, said means for rotating, and said means for axially moving are arranged coaxially with said central cylinder axis;

whereby manipulation of said means for rotating causes rotation of said cutting knife and separate manipulation of said first means causes axial movement of said cutting knife and, during a corneal disc excision operation, said means for rotating and said first means are at all times and in all positions accessible and independently manipulatable by an operator.

* * * * *